(12) United States Patent
Feldman et al.

(10) Patent No.: US 8,492,419 B2
(45) Date of Patent: Jul. 23, 2013

(54) MULTIFUNCTIONAL SOLID FORMULATIONS FOR WATER CONDITIONING

(75) Inventors: David Feldman, Haifa (IL); Theodore M. Fishler, Haifa (IL); Amiram Groweiss, Caesarea (IL); Aharon Weissman, Doar-Na Misgav (IL); Gideon Shikolsky, Kiryat-Motzkin (IL); Moshe Link, Haifa (IL)

(73) Assignee: Bromine Compounds Ltd., Beer-Sheva (IL)

( * ) Notice: Subject to any disclaimer, the term of this patent is extended or adjusted under 35 U.S.C. 154(b) by 350 days.

(21) Appl. No.: 12/226,723

(22) PCT Filed: Apr. 25, 2007

(86) PCT No.: PCT/IL2007/000512
§ 371 (c)(1),
(2), (4) Date: Jan. 5, 2009

(87) PCT Pub. No.: WO2007/122625
PCT Pub. Date: Nov. 1, 2007

(65) Prior Publication Data
US 2009/0220559 A1 Sep. 3, 2009

Related U.S. Application Data

(60) Provisional application No. 60/794,882, filed on Apr. 26, 2006.

(51) Int. Cl.
*C02F 1/76* (2006.01)
*A01N 25/00* (2006.01)

(52) U.S. Cl.
USPC .......... 514/389; 424/405; 424/661; 510/381; 252/175

(58) Field of Classification Search
USPC ... 210/753, 754, 756, 764; 252/175; 424/405, 424/613, 614, 615, 661, 662, 665; 510/367, 510/374, 375, 376, 377, 378, 379, 381; 514/389
See application file for complete search history.

(56) References Cited

U.S. PATENT DOCUMENTS

| | | | |
|---|---|---|---|
| 4,389,318 A | 6/1983 | Wojtowicz | |
| 5,614,528 A | 3/1997 | Jones et al. | |
| 5,854,189 A * | 12/1998 | Kruse et al. | 510/224 |
| 5,972,864 A * | 10/1999 | Counts | 510/367 |

(Continued)

FOREIGN PATENT DOCUMENTS

| | | | |
|---|---|---|---|
| GB | 1570361 A * | 7/1980 | |
| JP | 2003-160417 | 6/2003 | |

(Continued)

OTHER PUBLICATIONS

Kester et al. "Sodium, Magnesium, and Calcium Sulfate Ion Pairs in Seawater at 25C," Limnology and Oceanography, vol. 14, No. 5 (Sep. 1969) (p. 686 including abstract, only).*

(Continued)

*Primary Examiner* — Lucas Stelling

(57) ABSTRACT

Solid formulations for use in water conditioning of circulating reservoirs, processes of preparing same and methods for water conditioning utilizing same are disclosed. The solid formulations combine a sanitizer with a bath salt and/or an odoriferous substance.

5 Claims, 2 Drawing Sheets

U.S. PATENT DOCUMENTS

| | | | | |
|---|---|---|---|---|
| 6,294,510 | B1* | 9/2001 | Norman et al. | 510/381 |
| 2002/0187907 | A1* | 12/2002 | Mente et al. | 510/220 |
| 2003/0156981 | A1 | 8/2003 | Mills | |
| 2004/0164029 | A1 | 8/2004 | Souter et al. | |
| 2005/0279971 | A1 | 12/2005 | Garris | |
| 2009/0220559 | A1 | 9/2009 | Feldman et al. | |

FOREIGN PATENT DOCUMENTS

| | | |
|---|---|---|
| RU | 2093142 | 10/1997 |
| RU | 2007996 | 2/2004 |
| WO | WO 01/53214 | 7/2001 |
| WO | WO 03/044154 | 5/2003 |
| WO | WO 2006/009554 | 1/2006 |

OTHER PUBLICATIONS

International Search Report Dated Sep. 15, 2008 From the International Searching Authority Re.: Application No. PCT/IL07/00512.

Written Opinion Dated Sep. 15, 2008 From the International Searching Authority Re.: Application No. PCT/IL07/00512.

International Preliminary Report on Patentability Dated Jan. 22, 2009 From the International Bureau of WIPO Re.: Application No. PCT/IL2007/000512.

Office Action Dated Dec. 26, 2011 From the Israel Patent Office Re. Application No. 194855 and Its Translation Into English.

Supplementary European Search Report and the Europan Search Opinion Dated Apr. 11, 2012 From the European Patent Office Re. Application No. 07736252.3.

Iwasaki et al. Database WPI, XP002672434, AN 2003-793191, Week 200375.

Litkovskii et al. Database WPI, XP002672436, AN 1998-269955, Week 199824.

Pleskovskii et al. Database WPI, XP002672435, AN 1994-277474, Week 199434.

Communication Pursuant to Rules 70(2) and 70a(2) EPC Dated May 2, 2012 From the European Patent Office Re. Application No. 07736252.3.

Communication Pursuant to Article 94(3) EPC Dated Jan. 28, 2013 From the European Patent Office Re. Application No. 07736252.3.

Requisition by the Examiner Dated Feb. 28, 2013 From the Canadian Intellectual Property Office Re. Application No. 2,648,660.

* cited by examiner

MULTIFUNCTIONAL SOLID FORMULATIONS FOR WATER CONDITIONING

RELATED APPLICATIONS

This Application is a National Phase of PCT Patent Application No. PCT/IL2007/000512 having International filing date of Apr. 25, 2007, which claims the benefit of U.S. Provisional Patent Application No. 60/794,882 filed on Apr. 26, 2006. The contents of the above Applications are all incorporated herein by reference.

FIELD AND BACKGROUND OF THE INVENTION

The present invention relates to the field of water treatment and, more particularly, to novel compositions for treating (e.g., disinfecting and conditioning) water in circulating reservoirs such as pools, spas, hot-tubs, whirlpool bathtubs and similar structures.

Water reservoirs which are used by humans for bathing, e.g., for sports, recreational, therapeutic, hygienic, decorative and/or ceremonial purposes, require standing by certain mandatory, regulatory, customary and fashionable criteria. These include health related criteria which deal mostly with controlling pathogens of biological sources and the chemical composition of the water. Health criteria ensure that the water is effectively free of microbes and harmful substances which are responsible for acute and chronic human illness, and is environmentally safe. Other criteria deal with elements of choice and aesthetics such as taste, color, turbidity, odor and pH.

Typical water treatments employ physical, chemical, and biological procedures, and any combinations thereof, which are aimed at providing the water with the required and desired qualities. Chemical treatment of water includes conventional use of chemicals such as oxidizing and non-oxidizing biocides, algaecides, sanitizers, disinfectants, pH and alkalinity adjusters, dispersants, surfactants, corrosion and fur (scale) control agents, fouling control agents and deodorizing, odorizing and colorizing agents. Physical treatment of water includes filtration, aeration, irradiation, sedimentation and subjection to electromagnetic fields. Biological treatment of water, which is less common with water reservoirs used for bathing, includes enzymatic treatment and maintenance of a desired ecologic balance by means of microflora and higher species. Still, the predominant method for water treatment is based on a combination of filtration and chemical treatment.

The chemical treatment is typically a part of an overall water maintenance, treatment, conditioning and purification program, in which the required chemicals are usually added independently. The water is monitored periodically, following several parameters of the water quality, and when a particular parameter deviates from the acceptable range, the appropriate amount of the necessary chemical is added. Usually, adjusting one water quality parameter influences another water quality parameter. Therefore, conventional chemical water treatment and conditioning requires continuous balancing procedures which include monitoring the water quality parameters and adjustment with appropriate dosing of various chemicals to create and maintain the required and desired water quality.

Without this treatment, bacteria and algae may flourish uncontrollably and rather quickly in the water, especially in circulating reservoirs, and more so in those which are kept at an elevated temperature, such as heated swimming pools which are kept at 24-27° C., and hot-tubs and spas which are kept at 38-40° C.

Usually water quality improvement via chemical treatments is achieved by treating the water with strong oxidizers and/or active-halogen containing sanitizers. "Active halogen" is a phrase which is used herein to describe $Cl^+$ and $Br^+$, also known and referred to in the art as "free halogens" or "available halogens". Active halogens are known as highly effective antimicrobial agents, having a wide biocidal activity (e.g., antibacterial, antifungal, antialgal and antiviral activities), and thus are routinely used in water treatment systems.

Hypochlorous and hypobromous acids (HOCl and HOBr respectively) are common sources of active halogen and are frequently used as aggressive oxidizing and sanitizing agents for various applications, including water treatment systems. Hypochlorite and hypobromite ions are less effective sanitizers than the corresponding acids, therefore the pH of the water is maintained so as to favor a high concentration of the acid and a low concentration of the ions.

Other strong oxidizers that are typically used in water treatment include, for example, sodium- or potassium-persulfate, and sodium- or potassium-monopersulfate.

However, direct use of halogens and other strong oxidizers is limited as a result of the complications which arise from practical issues such as handling, storage, transport and disposal thereof, mainly due to their high reactivity and aggressiveness as oxidizing agents. Therefore, the use of compounds that are capable of releasing or generating active chlorine and/or bromine upon contact with water, and thus act as indirect oxidizing agents, is preferred. Moreover, hypochlorous and hypobromous acids are highly reactive and hence the concentration thereof diminishes rapidly due to consumption during reactions with the organic compounds and matter introduced to the water by bathers. Furthermore, hypochlorous and hypobromous acids deplete and readily decomposes into inactive breakdown products, such as hydrochloric acid or hydrobromic acid, water and oxygen, via UV radiation driven photochemical reactions upon exposure to direct sun light, and/or upon exposure to moderate and high temperatures, and thus require constant replenishment and the use of chemical stabilizers in order to control these effects and preserve the effectiveness of these sanitizers. The need for constant addition of sanitizers and stabilization thereof is greater still when the water of the circulating reservoir is kept at an elevated temperature, such as in hot-tubs and whirlpool bathtubs which are kept at 38-40° C., wherein the processes by which the chemicals are degraded and evaporate is hastened.

Hence, chemical compounds, such as trichloroisocyanuric acid (TCCA), sodium dichloroisocyanurate, 1-bromo-3-chloro-5,5-dimethylhydantoin, 1-chloro-3-bromo-5,5-dimethylhydantoin, 1-bromo-3-chloro-5-methyl-5-ethylhydantoin, 1-chloro-3-bromo-5-methyl-5-ethylhydantoin, 1-bromo-3-chloro-5,5-diethylhydantoin, 1-chloro-3-bromo-5,5-diethylhydantoin, 1-bromo-3-chloro-5-ethyl-5-methylhydantoin, 1-chloro-3-bromo-5-ethyl-5-methylhydantoin, 1,3-dichloro-5-ethyl-5-methylhydantoin, 1,3-dibromo-5-ethyl-5-methylhydantoin, 1,3-dichloro-5-methyl-5-ethylhydantoin, 1,3-dibromo-5-methyl-5-ethylhydantoin, 1,3-dichloro-5,5-dimethylhydantoin, 1,3-dibromo-5,5-dimethylhydantoin, 1,3-dichloro-5,5-diethylhydantoin, 1,3-dibromo-5,5-diethylhydantoin, any combination thereof and various, more rapidly dissolving salts thereof, are the major and most commonly used sanitizers in circulating reservoirs. These compounds combine the release of active halogen disinfectant agents together with the protective action thereof, when coming in contact with water, and ensure that the water remains clean and safe for the bathers (see, for example, release and stabilization of hypochlorous and hypobromous acids by 3-bromo-1-chloro-5,5-dimethylhydantoin in Scheme 1 below).

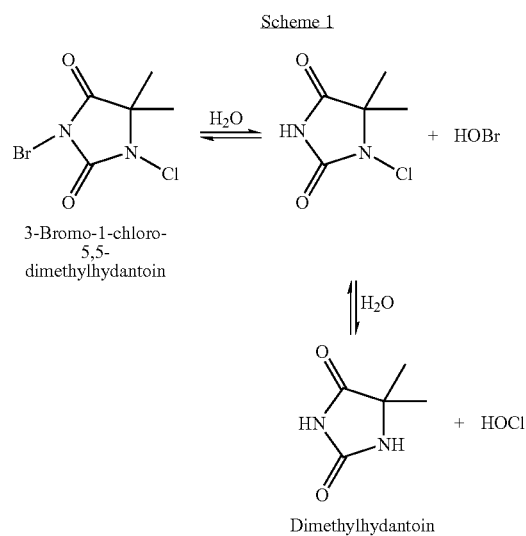

Scheme 1

3-Bromo-1-chloro-5,5-dimethylhydantoin

Dimethylhydantoin

However, these active-halogen generating sanitizers, and especially the products of their interactions with protein-based residues and various organic amines present in water, add unpleasant odors to the water and hence to the surrounding of the reservoir containing the water. These malodorous substances have an intensified impact in heated water of spas and hot-tubs due to their volatility.

Other than guarding the quality of water, and thus guarding the users of a circulating reservoir against microorganisms, active-halogen generating sanitizers, which addition thereof is considered compulsory, do not have any other beneficial effect, such as soothing, nurturing and/or healing qualities, on the well-being of the bathers. These highly desired qualities have been sought by humans for centuries.

In order to achieve such qualities, other chemical additives are optionally added to circulating reservoirs. Such chemical additives are aimed at improving the life quality of the bathers and in some cases treat health issues such as skin ailments, inflammation, pain, general physical infirmity and other physiological conditions as well as stress, fatigue, exhaustion and other mental conditions.

Bathing therapies have been known as early as the times of ancient Egypt and the Roman empire, where wealthy families availed themselves of "scented and anointed waters" to allegedly alleviate a virtual panoply of diseases, from minor muscular discomfort to life-threatening disease. This activity, which also provided the scene for social interactions, took place in natural hot springs and mineral springs as well as in man-made reservoirs. In modern times, many people of common standing can avail themselves with such pleasures or needs in public or privately owned circulating reservoirs, such as hot-tubs, whirlpool bathtubs and spas, without the need to travel to remote and scarce locations.

The most commonly and traditionally used additives for water in circulating reservoirs, which allow simulating the conditions found in natural hot and mineral springs, are bath salts. Bath salts are known as useful for relaxation, medicinal therapy and aromatherapy for many years. Modern bath therapies involve the use of commercially available salts, such as those found in sea salt and epsom salt, primarily comprised of various ion pairs of sodium, magnesium, potassium, calcium, chloride, bromide and sulfate.

Commercially available bath salts include, for example, Carnallite, which is an evaporite mineral comprising hydrated potassium magnesium chloride ($KMgCl_3.6(H_2O)$), other Dead-Sea salt products typically comprising water (about 36.4%), magnesium chloride (about 33.3%), potassium chloride (about 24.3%), sodium chloride (about 5.5%), bromide (about 0.5%), calcium chloride (about 0.2%), sulfates (about 0.15%) and insolubles (about 0.03%), and other sea and oceanic salts optionally formulated along with other minerals.

Bath salts are typically hygroscopic at ambient temperatures and hence handling, packaging, storage and usage thereof are inconvenient and require special conditions and treatment, which influences their commercial utility. For example, Carnallite, as well as other bath salts which are based on Carnallite, are so hygroscopic, that their intense tendency to adsorb water from the surrounding air will transform a solid, dry sample into a concentrated solution if left in contact with the ambient atmosphere. Camallite-based products are therefore packed in tightly sealed packages until used.

Commercially available bath salts are typically upgraded by the addition of odoriferous substances, which bestow a pleasant feeling to those using the water reservoir. Modern and traditional odoriferous substances include essential aromatic oils and other natural and modified extracts from plants and animals, as well as synthetic fragrances and perfumes. Odoriferous substances which can be used in bathing water are taught in, for example, U.S. Pat. Nos. 3,963,648, 4,051,076, 4,917,891 and 6,426,325. Other suitable essential oils and aromatic substances, such as wintergreen oil, clove oil, nutmeg oil, anise oil, vanilla oil, thyme oil, mint oil, sassafras oil, rose oil, orange oil, pine oil, rosewood oil, eucalyptus oil, ylang-ylang oil, lavender oil, patchouli oil and musk oil, are of traditional and folkloric origins and are readily available.

However, while most odoriferous substances are considered benign and even beneficial for use as additives in circulating reservoirs which are used for human bathing, blending of odoriferous substances with strong oxidizing agents, such as those generating active halogens, may result in a baneful oxidation of the odoriferous substances; leading to diminishing beneficial effects. In order to reduce the likelihood for this incompatibility, great care is practiced in the choice of stable odoriferous substances, and careful planning of their storage, formulation and addition thereof.

Other compatibility and safety issues become crucial when dealing with the use and storage of different water treatment chemicals, some of which are toxic, aggressive and highly reactive upon exposure to air, moisture and one with another. For example, oxidizers and other chemicals that are added to circulating reservoirs are often not compatible when blended with each other and hence the activity of the oxidizer or sanitizer can rapidly diminish as a result of such a mingle. Furthermore, while some water treatment chemicals are required to reach a final desired concentration rapidly and adjacently upon commencement of use of the water such as "pool-shock" products (aimed at rapid oxidative breakdown of water-soluble bather waste) and bath salts, other chemicals, such as halogen-releasing compounds and volatile odoriferous substances, are infused slowly and throughout the time period of use. Therefore, treating and maintaining the water of a circulating reservoir is characterized by a delicate balance of demand, stability, compatibility and solubility.

Difference in solubility alone may undermine the objectives of the water treatment plan if not considered and addressed.

It becomes evident that an overwhelmingly large number of chemicals force the average owner/proprietor/operator of a circulating reservoir, even a relatively small one, to spend considerable time and resources to maintain a wide spectrum of chemicals and to determine when, how much and for what purpose each of these chemicals must be added to the water system. In addition, substantial understanding of chemistry is required so as to avoid hazards, damages and inefficiency, as a result of an inadequate chemical treatment.

However wishful, an "all-in-one" multifunctional product for general reservoir maintenance that would prevent flawed used while still providing all the desired functions and benefits of water treatment is chemically and practically difficult to achieve in view of the limitations discussed hereinabove and thus is not yet available to consumers. Nevertheless, a product with even a partial multifunctionality would have great value in easing the task of maintaining water that requires such chemical treatment and conditioning.

Some non-obvious formulations and multifunctional products for water treatment are known, and include, for example, sanitizing, cleansing and refreshing products for use in toilet bowls, dishwashers, swimming pools, spas and other home and industrial water applications.

For example, while bath salts and odoriferous substances are often sold and used separately, thus adding to the already large number of water-maintenance chemicals mentioned above, some compositions such as those taught in, for example, U.S. Pat. No. 5,958,462, combine bath salts and essential oils into one product.

Other multifunctional products containing combined water treatment chemicals, especially those which include an oxidizer/sanitizer component, may actually be based on the differences in solubility of various chemicals so as to address the differences in the demanded administration thereof. Products which are based on compacting various water treatment chemicals having dissimilar solubility in different layers are disclosed in, for example, U.S. Pat. Nos. 3,873,685 and 6,863,830, which teach the combination of several layers in one tablet wherein one layer contains a fast dissolving halogen-releasing agent while a second layer provides a slower dissolving halogen-releasing agent. Various geometric shapes of tablets are suggested in these patents, wherein the discrete portions of the ingredients are provided in structures having either a layered structure or an inner core and outer core such as in the shape of a rod or oval ball. These products deliver sanitizers and stabilizers; however they fail to provide other highly sought qualities and benefits as discussed hereinabove, such as those obtained from chemicals such as odoriferous substances and bath salts.

Yet other multifunctional products, such as those taught in U.S. Pat. No. 6,852,238, are aimed at a safe and effective combination of two incompatible chemicals: a halogen source and a pH compensating source, in the form of a multi-layered tablet. The water treatment composition described in this patent comprises a multi-layer tablet wherein one discrete layer contains at least one halogen source and a second discrete layer contains at least a pH compensating source. Still these products fail to provide other highly sought qualities and benefits.

In an attempt to avoid oxidation of an odoriferous substance by a sanitizing substance as mentioned hereinabove, U.S. Pat. No. 5,759,974 and EP 1553162 disclose lavatory cleansing and freshening blocks, having a layer or a core comprising one substance and a layer or a shell comprising the other substance. While these disclosures teach the combination of two chemically and physically incompatible substances, they fail to teach water treatment products which are suitable for human bathing, and which include other chemicals such as bath salts.

U.S. Pat. No. 6,617,297 discloses automatic dishwashing tablets with improved chlorine stability, stemming from the use of certain nonionic surfactants in machine dishwashing detergent tablets containing chlorinating agents. This disclosure also fails to teach formulations which are suitable for human bathing.

U.S. Pat. No. 5,256,328 discloses a liquid toilet bowl cleaning and sanitizing composition comprising an aqueous dispersion of particles of at least one halogen donating compound. Other than teaching a liquid composition, which is unsuitable for the chemicals which are used in water treatment of circulating reservoirs, this disclosure also fails to teach formulations which are suitable for human bathing.

Other multifunctional products of various detergents and sanitizers are taught in, for example, U.S. Pat. Nos. 4,731,195 and 6,174,192, yet, these patents are not directed at products for circulating water reservoirs designed for human bathing as mentioned above, and hence none addresses the issues of combining reactive sanitizers, with beneficial substances such as the hygroscopic bath salts and/or the volatile and oxidation prone odoriferous substances.

There is thus a widely recognized need for, and it would be highly advantageous to have multifunctional formulations, which can conveniently provide a combination of desired chemicals to water of circulating reservoirs.

SUMMARY OF THE INVENTION

The present invention relates to the field of water treatment and, more particularly, to novel solid compositions for treating, namely disinfecting and conditioning water in circulating reservoirs such as pools, spas, hot-tubs, whirlpool bathtubs and similar structures, containing a chemically stable admixture of sanitizers and bath salts and/or odoriferous substances, formed in mechanically stable compacted bodies.

Thus, according to one aspect of the present invention there is provided a solid formulation which comprises one or more sanitizers and one or more bath salts, the formulation being identified for use in water conditioning.

According to further features in preferred embodiments of the invention described below, the solid formulation further comprises one or more odoriferous substances.

According to another aspect of the present invention there is provided a process of preparing the solid formulation described above, the process comprising admixing the sanitizer(s) and the bath salt(s) to thereby obtain a first admixture.

According to further features in preferred embodiments of the invention described below, the process further comprises, prior to the admixing, drying the bath salt.

According to still further features in preferred embodiments of the invention the drying is partial.

According to further features in preferred embodiments of the invention described below, the process further includes compacting the first admixture.

According to still further features in preferred embodiments of the invention the compacting process is effected by a procedure selected from the group consisting of pressing, extrusion and molding, preferably pressing.

According to still further features in preferred embodiments of the invention the compacted body is layered, and the process further includes, prior to the admixing, compacting the sanitizer to thereby form a first layer and compacting the bath salt on top of the first layer to thereby form a second layer.

According to still further features in preferred embodiments of the invention the formulation further comprises one or more odoriferous substances, and the process further comprises, prior to the admixing, blending the bath salt with the odoriferous substance to thereby obtain a second admixture and admixing the second admixture with the sanitizer to thereby obtain a third admixture.

According to still further features in preferred embodiments of the invention the formulation has a form of a compacted body and the process further includes compacting the third admixture, as described herein.

According to further features in preferred embodiments of the invention described below, the compacted body is layered and the process further includes, prior to the admixing, compacting the sanitizer to thereby form a first layer and compacting the second admixture on top of the first layer to thereby form a second layer.

According to yet another aspect of the present invention there is provided a solid formulation which comprises one or more sanitizers and one or more odoriferous substances, the formulation being identified for use in water conditioning.

According to still another aspect of the present invention there is provided a process of preparing the solid formulation described above, the process comprises blending the sanitizer and the odoriferous substance to thereby obtain a fourth admixture.

According to further features in preferred embodiments of the invention described below, blending and/or admixing the odoriferous substance with either the sanitizer or the bath salt or a mixture thereof is effected by spraying the odoriferous substance over the sanitizer, the bath salt or the mixture thereof.

According to further features in preferred embodiments of the invention described below, the formulation has a form of a compacted body and the process further includes compacting the fourth admixture preferably by pressing, extrusion or molding, and more preferably, by pressing.

According to further features in preferred embodiments of the invention described below, the water conditioning comprises conditioning water in a circulating reservoir.

According to still further features in preferred embodiments of the invention the circulating reservoir is selected from the group consisting of a pool, a hot-tub, a whirlpool bathtub and a spa.

According to still further features in preferred embodiments of the invention the solid formulations presented herein have a mechanical strength that ranges from about 10 N/cm$^2$ to about 70 N/cm$^2$. Accordingly, the solid formulations presented herein have a breaking force that ranges from about 50 N to about 300 N, preferably from about 100 N to about 300 N.

According to still further features in preferred embodiments of the invention the solid formulations presented herein are chemically stable upon storage for a time period of at least 7 days.

According to still further features in preferred embodiments of the invention a change in a water content of the solid formulations upon the storage is less than 3 weight percents of the total weight of the solid formulation.

According to still further features in preferred embodiments of the invention the storage is effected at a temperature that ranges from about 0° C. to about 50° C.

According to still further features in preferred embodiments of the invention the storage is effected at an ambient humidity that ranges from about 20% to about 65%.

According to further features in preferred embodiments of the invention described below, the solid formulations presented herein have a form of a compacted body.

According to still further features in preferred embodiments of the invention the morphology of the compacted body is selected from the group consisting of a prill, a nugget, a flake, a granule, a pellet, a pill, a caplet, a tablet, a wafer, a briquette, a puck and a block.

According to still further features in preferred embodiments of the invention the morphology of the compacted body is selected from the group consisting of a pill, a caplet, a tablet, a wafer, a briquette, a puck and a block.

According to still further features in preferred embodiments of the invention the compacted body has a shape selected from the group consisting of a box, a sphere, a cube, an ellipsoid, a cylinder, a bar, a cone, a pyramid, a frustum, a prism and a torus.

According to further features in preferred embodiments of the invention described below, the solid formulations presented herein have a layered structure.

According to further features in preferred embodiments of the invention described below, the amount of the sanitizer in the formulations described herein ranges from about 1 weight percentages to about 99.99 weight percentages of the total weight of the solid formulation, as is detailed hereinunder.

According to still further features in preferred embodiments of the invention the sanitizer is selected from the group consisting of trichloroisocyanuric acid, sodium persulfate, sodium monopersulfate, sodium dichloroisocyanurate, potassium persulfate, potassium monopersulfate, lithium hypochlorite, calcium hypochlorite, 1-bromo-3-chloro-5,5-dimethylhydantoin, 1-chloro-3-bromo-5,5-dimethylhydantoin, 1-bromo-3-chloro-5-methyl-5-ethylhydantoin, 1-chloro-3-bromo-5-methyl-5-ethylhydantoin, 1-bromo-3-chloro-5,5-diethylhydantoin, 1-chloro-3-bromo-5,5-diethylhydantoin, 1-bromo-3-chloro-5-ethyl-5-methylhydantoin, 1-chloro-3-bromo-5-ethyl-5-methylhydantoin, 1,3-dichloro-5-ethyl-5-methylhydantoin, 1,3-dibromo-5-ethyl-5-methylhydantoin, 1,3-dichloro-5-methyl-5-ethylhydantoin, 1,3-dibromo-5-methyl-5-ethylhydantoin, 1,3-dichloro-5,5-dimethylhydantoin, 1,3-dibromo-5,5-dimethylhydantoin, 1,3-dichloro-5,5-diethylhydantoin, 1,3-dibromo-5,5-diethylhydantoin, salts thereof and combinations thereof.

In a preferred embodiment, the sanitizer is BCDMH, as defined hereinafter.

According to further features in preferred embodiments of the invention described below, the content of the bath salt, if present, in the formulations described herein ranges from about 1 weight percentage to about 95 weight percentages of the total weight of the solid formulation, as is detailed hereinunder.

According to still further features in preferred embodiments of the invention the bath salt is selected from the group consisting of Camallite, a sea salt, an oceanic salt, a sodium containing salt, a potassium containing salt, a magnesium containing salt, a calcium containing salt, zinc containing salt, a tin containing salt, a manganese containing salt, a chloride containing salt, a bromide containing salt, a sulfate containing salt, a phosphate containing salt and any combinations thereof. In a preferred embodiment, the bath salt is Camallite, as defined hereinafter.

According to further features in preferred embodiments of the invention described below, the content of the odoriferous substance, if present, ranges from about 0.001 weight percentage to about 5 weight percentage of total weight of the solid formulation.

According to still further features in preferred embodiments of the invention the odoriferous substance is selected from the group consisting of anise oil, cineol, clove oil, eucalyptus oil, lavender oil, mint oil, musk oil, nutmeg oil, orange oil, patchouli oil, phenethyl acetate, pine oil, rose oil, rosewood oil, sassafras oil, thyme oil, vanilla oil, wintergreen oil, ylang-ylang oil, and any combinations thereof.

According to further features in preferred embodiments of the invention described below, the solid formulation further comprises one or more additional ingredients selected from the group consisting of an inorganic base, a transdermally active therapeutic agent, a therapeutic agent active by inhalation, a skin conditioning agent, a sunscreen, a buffering agent, a chelating agent, a clarifier, a colorant, a dye, a pearlescent agent, a flocculent, a corrosion inhibitor, a disintegrant, a dispersant, a dissolution control agent, a foaming agent, a fragrance, a perfuming agent, a pH-adjusting agent, a scale inhibitor, a sequesterant, a surface-active agent, a surfactant, a UV blocking agent, a water softener, an algaecide, an algaestat, an antifoaming agent, an oil and any combinations thereof.

According to still further features in the preferred embodiments, the solid formulation further comprises an inorganic base, whereby the inorganic base is selected from the group consisting of calcium hydroxide, sodium carbonate, sodium bicarbonate, calcium oxide, potassium hydroxide, magnesium oxide, magnesium hydroxide and sodium hydroxide. Preferably, the inorganic base is calcium hydroxide and/or sodium carbonate. Such formulations can be in the form of, for example, granules or pellets.

According to still further features in preferred embodiments of the invention the concentration of the additional ingredient ranges from about 0.001 weight percentage to about 5 weight percentages of total weight of the solid formulation.

According to an additional aspect of the present invention there is provided a method of conditioning water of a circulating reservoir, the method comprising contacting the water with the solid formulation presented herein.

According to further features in preferred embodiments of the invention described below, the circulating reservoir is selected from the group consisting of a pool, a hot-tub, a whirlpool bathtub and a spa.

According to still further features in preferred embodiments of the invention the method further comprises placing the solid formulation in an erosion feeder which forms a part of the circulating reservoir.

The present invention successfully addresses the shortcomings of the presently known configurations by providing chemically and physically stable solid formulations combining sanitizers with bath salts and/or odoriferous substances, which are highly suitable for use in water conditioning and which are far superior to the presently used formulations by exhibiting health-care functionality (e.g., sanitizing properties) while further contributing to the well-being of bathers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
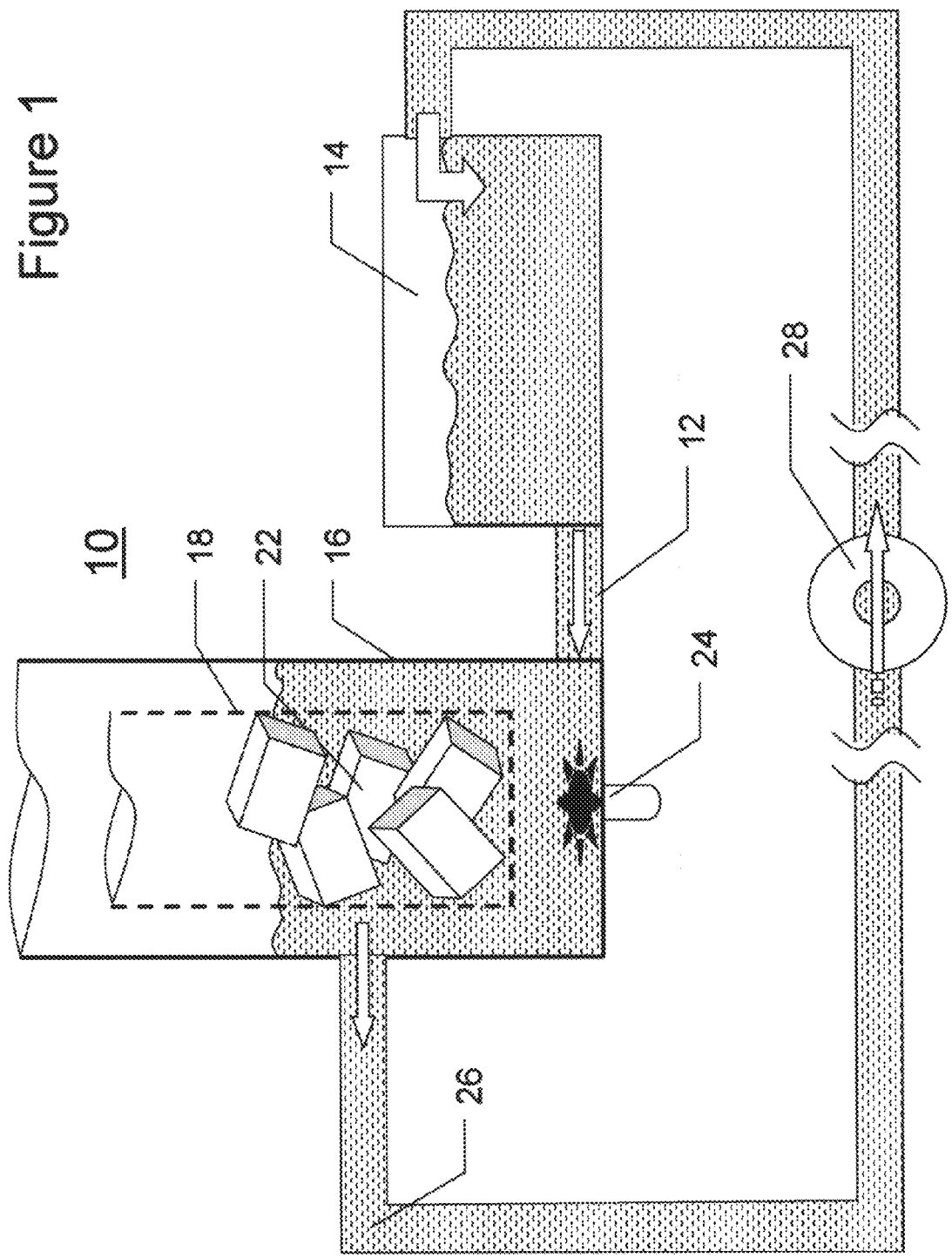
FIG. 1 presents a schematic illustration of an erosion feeder comprising a perforated basket, in which the solid formulations according to the present invention in the form of granules, pellets, tablets or pucks (represented by box-shaped tablets for clarity) are placed, inserted in a dissolution tank through which water flows by force of a pump so as to dissolve (erode) the solid formulations and thereby impart the chemicals of the formulations to the water of a circulating reservoir.

The present invention relates to the field of water treatment and, more particularly, to novel compositions for treating (e.g., disinfecting and conditioning) water in circulating reservoirs such as pools, spas, hot-tubs, whirlpool bathtubs and similar structures. The novel compositions presented herein are solid formulations containing a chemically stable admixture of sanitizers with bath salts and/or odoriferous substances.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, water of circulating reservoirs, especially those used for bathing by humans, must be treated so as to prevent the development of microorganisms, adjust the pH of the water and maintain a pleasant look and scent. The compulsory tasks of disinfection and filtration are typically performed by sanitizers (typically halogen-releasing chemicals) which are dispensed automatically or manually, and a variety of filtering devices for removal of particulates. Other chemicals are used for pH adjustments, water-softness adjustments, lucidification, corrosion and scale prevention and the likes.

In addition to the compulsory maintenance of a circulating reservoir, other benefits such as soothing, nurturing and/or healing activities can be effected for the well-being of the bathers, especially in small, heated circulating reservoirs such as hot-tubs, spas and heated whirlpools. These highly desired benefits can be achieved by adding chemicals such as bath salts, odoriferous substances, coloring agents and other water conditioning additives.

As further discussed hereinabove, water treatment requires constant monitoring and replenishment of the abovementioned chemicals so as to maintain the desired chemical balance and beneficial effects thereof, as some compounds are spent, degrade and evaporate from the water, and more so in heated reservoirs. This non-trivial task of water reservoir maintenance involves the use of a multitude of chemicals, some of aggressive nature, which must be used in specific dosages, combinations and timing. The requirement for a certain order of addition and the inclination of some chemicals to degrade due to ambient conditions such as humidity, oxygen, UV and heat, or otherwise cross-react with one another forbids the creation of "all-in-one" formulations for total water treatment. Still, even partial multifunctional formulations, put in one "user-friendly" product, would have great value in easing the task of maintaining water that requires such chemical treatment and conditioning.

While attempting the non-trivial task of developing multifunctional formulations for water treatment and conditioning, the present inventors have surprisingly found that in spite of the hygroscopicity of bath salts, the reactive nature of halogen-releasing sanitizers and the chemical sensitivity of fragrances, a combination of some or all of these chemicals in one admixture results in chemically viable and stable formulations. Moreover, it was surprisingly found that compacting these formulations into packed bodies of various forms further increases the stability thereof in terms of moisture absorption, oxidation and decomposition.

Thus, according to one aspect of the present invention, there are provided solid formulations, being particularly useful in water conditioning, each comprising one or more sanitizers and one or more bath salts.

The phrase "solid formulation", as used herein, refers to a mixture of various chemical substances, all of which are in solid state at room temperature when separate and when mixed together. A solid formulation can consist of fine, small, coarse or large particles, or form large bodies of various shapes by various industrial techniques.

The term "sanitizer" or "disinfectant", as used herein, refers to a chemical agent that destroys disease-causing microorganisms and other forms of microscopic water dwelling biota and spores thereof that impair the desired properties of water, such as odor, clarity and color. Sanitizers, disinfectants or germicides, are considered to be substances applied to inanimate bodies as opposed to antiseptics which are used to kill microorganisms in or on living things. Chlorine-, bromine- and iodine-releasing compounds are the most commonly used disinfectants. Diluted solutions of some disinfecting chemicals, such as the water of a swimming pool or a hot-tub, may come in contact with human skin. Non-limiting examples of sanitizers that are suitable for use in the context of the present invention include trichloroisocyanuric acid, sodium persulfate, sodium monopersulfate, sodium dichloroisocyanurate, potassium persulfate, potassium monopersulfate, lithium hypochlorite, calcium hypochlorite, 1-bromo-3-chloro-5,5-dimethylhydantoin, 1-chloro-3-bromo-5,5-dimethylhydantoin, 1-bromo-3-chloro-5-methyl-5-ethylhydantoin, 1-chloro-3-bromo-5-methyl-5-ethylhydantoin, 1-bromo-3-chloro-5,5-diethylhydantoin, 1-chloro-3-bromo-5,5-diethylhydantoin, 1-bromo-3-chloro-5-ethyl-5-methylhydantoin, 1-chloro-3-bromo-5-ethyl-5-methylhydantoin, 1,3-dichloro-5-ethyl-5-methylhydantoin, 1,3-dibromo-5-ethyl-5-methylhydantoin, 1,3-dichloro-5-methyl-5-ethylhydantoin, 1,3-dibromo-5-methyl-5-ethylhydantoin, 1,3-dichloro-5,5-dimethylhydantoin, 1,3-dibromo-5,5-dimethylhydantoin, 1,3-dichloro-5,5-diethylhydantoin, 1,3-dibromo-5,5-diethylhydantoin, salts thereof and combinations thereof.

In a preferred embodiment, the sanitizer is BCDMH.

As is well-accepted in the art, the term "BCDMH", abbreviating "bromo-, chloro-dimethylhydantoin", is used herein to collectively describe any bromo-substituted and/or chloro-substituted derivative of 5,5-dimethylhydantoin. Thus, the term "BCDMH" encompasses any of 1-bromo-3-chloro-5,5-dimethylhydantoin, 1-chloro-3-bromo-5,5-dimethylhydantoin, 1,3-dichloro-5,5-dimethylhydantoin and 1,3-dibromo-5,5-dimethylhydantoin, either alone or in combination.

It is noted herein that in aqueous solutions, 1-bromo-3-chloro-5,5-dimethylhydantoin and 1-chloro-3-bromo-5,5-dimethylhydantoin are often both present in equilibrium. Further, commercially available bromo/chloro derivatives of 5,5- dimethylhydantoin typically include a mixture of 1-bromo-3-chloro-5,5-dimethylhydantoin, 1-chloro-3-bromo-5,5-dimethylhydantoin, 1,3-dichloro-5,5-dimethylhydantoin and 1,3-dibromo-5,5-dimethylhydantoin, mainly due to difficulties associated with separating the products formed in the industrial process.

"Bath salt" is a common name for a mixture of minerals originating from sea beds, off-shore and inland mines and evaporation plants, which is used as an additive to water of circulating reservoirs. Bath salts are traditionally attributed therapeutic and other beneficial influences on humans for centuries. Non-limiting examples of bath salts that are suitable for use in the context of the present invention include Camallite and Camallite-based salts, sea salts, oceanic salts, salts containing sodium, potassium, magnesium, calcium, zinc, tin, manganese, chloride, bromide, sulfate, phosphate and any combinations thereof. In a preferred embodiment, the bath salt is Carnallite.

As used herein, and is well-accepted in the art, Carnallite is a commercial product that comprises a mixture of KCl and $MgCl_2$ salts.

The compulsory use of sanitizers carry with it the most recognizable adverse effect identified with halogen-releasing chemicals: the undesired scent stemming from the active released substance. This malodorous scent can be masked in the presence of odoriferous substance.

Hence, according to preferred embodiments of this aspect of the present invention, the formulations described herein further include one or more odoriferous substance. Odoriferous substances may also be included in the formulations presented herein as an integral and principal ingredient in a comprehensive aromatherapeutic treatment which is effected in the water of a circulating reservoir treated with the present formulations.

The phrase "odoriferous substance", as used herein, refers to a chemical substance or a mixture of several substances of natural or synthetic origins, having or giving off an odor which is commonly conceived as pleasant. Thousands of odoriferous substances are known, and dozens of new odoriferous compounds emerge yearly. Traditional odoriferous substances include extracts and essential oils of natural origins, which are used as raw or refined materials. The most renowned odoriferous substances are essential oils, which are volatile oils that occur mostly in plants and give to the plants their characteristic odors, flavors, and other such properties. Essential oils are found in various parts of the plant body (in the seeds, flowers, bark, or leaves) and are also concentrated in certain special cells or groups of cells (glands).

Being natural products that exhibit these desired properties, essential oils are widely used in perfumes, flavorings and medicines. Their chemical composition spans terpenes, aldehydes, ketones, phenols and esters. In general, essential oils are complex mixtures which are obtained in various ways such as compression, distillation, extraction by dissolution or absorption, pressure and maceration.

Among the plants notable for their essential oils are members of the following plant families: carrot (e.g., anise, dill, angelica), ginger (cardamom), heath (wintergreen), laurel (cinnamon and camphor), mint (pennyroyal, peppermint, spearmint, thyme), myrtle (clove and eucalyptus), olive jasmine and lilac), orchid (vanilla), pulse (acacia and sweet pea), rose (attar of roses and almond), and rue (lemon and other citrus plants).

Non-limiting examples of odoriferous substances that are suitable for use in the context of the present invention include anise oil, cineol, clove oil, eucalyptus oil, pine oil, lavender oil, mint oil, musk oil, nutmeg oil, orange oil, patchouli oil, phenethyl acetate, rose oil, rosewood oil, sassafras oil, thyme oil, vanilla oil, wintergreen oil, ylang-ylang oil, and any combinations thereof. Particularly preferred odoriferous substances include eucalyptus oil and pine oil.

Alternatively, the odoriferous substance can be a synthetically prepared substance such as esters and ethers. An exemplary synthetic odoriferous substance is phenethyl acetate.

Alternatively, as described hereinabove, the sanitizer(s) can be admixed with the odoriferous substance(s) without the presence of a bath salt. Such solid formulations are advantageous for use in circulating reservoirs in which the malodorous nature of the sanitizers requires masking which is effected by the odoriferous substance(s). This is particularly advantageous when the formulations are used by private users, since the presence of the odoriferous substances renders the handling and use of a sanitizing formulation more pleasant.

Hence, according to another aspect of the present invention there are provided solid formulations, being identified for use in water conditioning, each comprising one or more sanitizers and one or more odoriferous substances, as detailed herein.

The phrase "water conditioning", as used herein, refers to a multifunctional treatment of water, and encompasses disinfecting the water, attributing beneficial traits thereto, such as adding desirable additives thereto, and generally maintaining the water at acceptable and desirable chemical conditions.

As discussed hereinabove, circulating water reservoirs, in which the water is not replaced frequently but rather undergo recirculation, are suitable for recreational and therapeutic uses which are effected by the addition of special beneficial chemicals. On the other hand, circulated water is more prone to microorganism infections and hence requires treatment with sanitizers and disinfectants. Therefore, according to preferred embodiments, the solid formulations presented herein are suitable for water conditioning in circulating reservoirs.

The phrase "circulating reservoir", as used herein, refers to a structure for holding a relatively large amount of water. The relatively large amount of water means that the water is not replaced after every use, or rarely replaced in general for a long period of time in terms of days, weeks and months, depending on the size of the reservoir and its preferred use, and hence maintaining the water is typically effected by a circulating procedure. In order to maintain the water, it is at least partially pumped or otherwise transferred out of the reservoir structure and then back into the reservoir by means of a water transferring device such as, for example, a pump, while being passed via a water treatment system. Typical water treatment system includes water treatment devices, such as, for example, heaters, coolers, chemical feeders, chemical exchangers and filters of various purposes and designs. These devices often form a part of a system which can include various combinations thereof, whereby the devices are further connected to control units such as sensors and detectors.

Exemplary circulating reservoirs for which the formulations described herein are suitable include public, private and home-based indoors or outdoors reservoirs which are used by humans for hygiene, sports, professional training, recreation, amusement, therapeutic and general bathing and for ceremonial and aesthetic purposes. These include, without limitation, pools, artificial ponds and lakes, swimming pools, spas, hot-tubs, whirlpool baths, fountains and waterslides. More preferably, circulating reservoirs according to the present invention are heated to elevated temperatures of 35° C. to 42° C., and include heated pools, hot-tubs, whirlpool bathtubs and spas.

The amounts of the various ingredients in the formulations according to the present embodiments affect the stability and effectiveness thereof.

According to preferred embodiments of the present invention, the total amount of the sanitizer(s) in each formulation ranges from about 1 weight percentages to about 99.99 weight percentages of the total weight of the solid formulation.

In formulations that are used primarily for disinfection purposes, preferably, the total amount of the sanitizer(s) in each formulation ranges from about 50 weight percentages to about 99.99 weight percentages of the total weight of the solid formulation. Thus, in such formulations the total amount of the sanitizer can be, for example, 50 weight percentages, 55 weight percentages, 60 weight percentages, 65 weight percentages, 70 weight percentages, 75 weight percentages, 80 weight percentages, 85 weight percentages, 90 weight percentages, 95 weight percentages, and even 99 weight percentages or higher. Such formulations are particularly advantageous for conditioning water in public water reservoirs.

Accordingly, the content of the bath salt(s), when present in such formulations, preferably ranges from about 1 weight percentage to about 50 weight percentages of the total weight of the solid formulation, preferably from about 5 weight percentages to about 30 weight percentages, and more preferably from about 5 weight percentages to about 15 weight percentages.

As used herein, the term "about" describes ±10%.

In cases where the solid formulations cater to the need to use bath salts under sanitizing conditions in a water reservoir, each formulation preferably comprises one or more types of a bath salt as the major component and one or more types of a sanitizer as the minor component. These formulations are particularly useful for conditioning water in private water reservoirs and preferably have a form of a granulated formulation. Such formulations may optionally further comprise an odoriferous substance.

In such formulations, the total amount of the bath salts(s) preferably ranges from about 50 weight percentages to about 95 weight percentages of the total weight of the solid formulation, preferably from about 70 weight percentages to about 90 weight percentages of the total weight of the formulation. Accordingly, the content of the sanitizer(s) in such formulations preferably ranges from about 1 weight percentages to about 50 weight percentages of the total weight of the solid formulation, preferably from about 10 weight percentages to about 30 weight percentages of the total weight of the solid formulation.

In each of the formulations described hereinabove, the content of the odoriferous substance(s), if present, depends on the desired effect of the solid formulation and its composition and structure, and can range from about 0.0001 weight percentage to about 5 weight percentage of the total weight of the solid formulation, preferably from about 0.001 weight percentage to about 1 weight percentage, more preferably from about 0.005 weight percentage to about 0.1 weight percentage, and most preferably from about 0.005 weight percentage to about 0.05 weight percentage.

As is demonstrated in the Examples section that follows, it has been surprisingly found that the solid formulations presented herein are chemically stable upon storage for a time period of at least 7 days, preferably of at least 30 days, and more preferably of at least 180 days.

The chemical stability of a product, such as its capacity to absorb moisture and/or degrade chemically, is crucial for its practicality and effectiveness, especially of a product which is comprised of sensitive and reactive chemicals, and affects the choice of packaging material, shipment and storage conditions, and the length of its "shelf-life".

The phrase "shelf life" as used herein, refers to the length of time that corresponds to a tolerable loss in quality of a perishable item or length of time a product may be stored without becoming unsuitable for use or consumption. Shelf life is related to the phrase "expiration date", wherein the first phrase typically relates to quality and the latter typically relates to safety. A product that has passed its shelf life is still safe, but optimal quality is no longer guaranteed. Shelf life is most influenced by five primary events: light transmission, gas transmission, heat transmission, humidity transmission, or mechanical stresses. Product quality is often mathematically modeled around a single parameter: the concentration of a chemical compound (such as the desired chemical or a degradation byproduct), a microbiological index, or a physico-mechanical parameter. Nearly all chemical reactions will occur (at various rates depending on the individual nature of the reaction) at common temperatures.

Examples of degradation byproducts that may affect the shelf life of the formulations presented herein include elemental halogen, which is released upon the breakdown of many halogen-releasing sanitizers.

These breakdown processes characteristically occur more rapidly at higher temperatures. Typically, chemical reactions double their rate for every 10° C. increase in the ambient temperature. As elevated temperature speeds up degradation reactions, temperature reductions reduce them.

The phrase "chemically stable", as used herein, refers to the ability of the formulations to remain chemically unchanged for the duration of a time period at typical storage conditions, and thus to preserve its desired qualities and the originally intended potential to exert certain beneficial effects. In the context of the present invention, chemical stability can be exhibited by low levels of moisture (water) absorption and low levels of chemical degradation products upon storage at typical conditions.

While storage conditions can affect the chemical stability of the formulations, it has been found that the formulations presented herein are chemically stable for a prolonged (at least 7 days) time period upon storage at a temperature that ranges from about 0° C. to about 50° C., preferably from about 0° C. to about 25° C., and at an ambient humidity that ranges from about 20% to about 65%, preferably from about 20% to about 45%.

In cases where the sanitizer is a halogen-releasing agent, the most indicative criterion of chemical stability is a low level of halogen which is released upon storage. In the case of brominating sanitizers, the absence or presence of visible red-brown fumes of elemental bromine can be used as an indication of the stability thereof.

Furthermore, since bath salts are typically hygroscopic and tend to absorb moisture from the ambient atmosphere when exposed thereto, another indicative criterion of the chemical stability of the formulations is a change in the water content of the solid formulations. The change in the water content of the solid formulations presented herein upon storage was found to be less than 3 weight percents of the total weight of the solid formulation. Such a minor change in the water content of a solid formulation that contains highly hygroscopic bath salts demonstrates one of the advantageous features of the formulations described herein. Thus, as opposed to bath salts formulations that should be handled and stored in strictly sealed packages due to their high hygroscopicity, the formulations described herein, being less susceptible to moisture absorption, are easier to handle.

As known in the art and disclosed in, for example, U.S. Pat. Nos. 5,780,641 and 6,680,070, solid formulations containing halogen-releasing sanitizers can be stabilized by the addition of an inorganic base such as dry calcium hydroxide.

While reducing the present invention to practice, it was further found that small amounts of alkaline chemicals, namely inorganic bases, such as, for example, sodium carbonate or calcium hydroxide, significantly increase the stability of the formulations presented herein at all physical shapes and forms. The presence of the inorganic base in the formulations presented herein can contribute to the chemical stability of the sanitizer. It is assumed that the presence of an alkaline compound prevents the formation of elemental halogen (e.g., bromine or chlorine). Since elemental halogen is typically formed upon degradation of the sanitizer under acidic conditions, the inorganic base suppresses acid formation and hence the release of elemental halogen.

Thus, according to preferred embodiments of the present invention, the solid formulations described herein further comprise an inorganic base. Representative examples of inorganic bases that are suitable for use in this context of the present invention include, without limitation, calcium hydroxide, sodium carbonate, sodium bicarbonate, calcium oxide, potassium hydroxide, magnesium oxide, magnesium hydroxide and sodium hydroxide.

Preferably, the amount of the inorganic base in the solid formulation ranges from about 0.01 weight percentage to about 5 weight percentages of the total weight of the solid formulation, more preferably from about 0.01 weight percentage to about 1 weight percentage, more preferably from about 0.1 weight percentage to about 1 weight percentage, and more preferably from about 0.1 weight percentage to about 0.5 weight percentage of the total weight of the solid formulation.

Formulations containing an inorganic base can be formulated as compacted bodies, as described hereinbelow. However, due to their improved stability, such formulations can optionally be formulated simply as granules or pellets.

Further to the chemical stability thereof, the physico-mechanical properties of a product, especially that which is comprised of a formulation of solid chemicals, are crucial for its manufacturing process as well as for its packaging, storage, shipment, marketing and use thereof. A particularly important feature in this respect is the mechanical strength of the product. Materials and formulations of several materials are "tested to destruction" under laboratory conditions. Objects made of these materials are deliberately overloaded with the particular force that acts against the property or strength to be measured, and changes in form are measured at high accuracy. These static tests are conducted to determine a material's elastic limit, ductility, hardness, reaction to temperature change, and other properties.

The solid formulations presented herein were found to be beneficially characterized by a mechanical strength that ranges from about 10 N/cm$^2$ to about 70 N/cm$^2$. Accordingly, the solid formulations presented herein are characterized by a breaking force that ranges from about 50 N to about 300 N, preferably from about 100 N to about 300 N.

Further, the solid formulations presented herein were found to exhibit such a mechanical strength during a prolonged time period. As is demonstrated in the Examples section that follows, in formulations that comprise a sanitizer and an odoriferous substance, the mechanical strength (or breaking force) of the solid formulations was even improved upon storage (see, Table 2 below), whereby in other formulations, no significant change was observed in the mechanical strength (or breaking force) upon storage.

The phrases "mechanical strength" and "breaking force", as used herein, are synonymous with similar terms such as hardness, firmness, sturdiness or fastness, and refer to the ability and reliability of an object to resist breakage and withstand pressure, force, or stress applied thereto. There are several methods for measuring the capability of matter to resist breakage, such as applying scalable starching and/or pressing forces to the object while monitoring various transitions, shifts and other mechanical changes which occur to the object as a result of the recorded level of the applied force(s).

Figure 2:
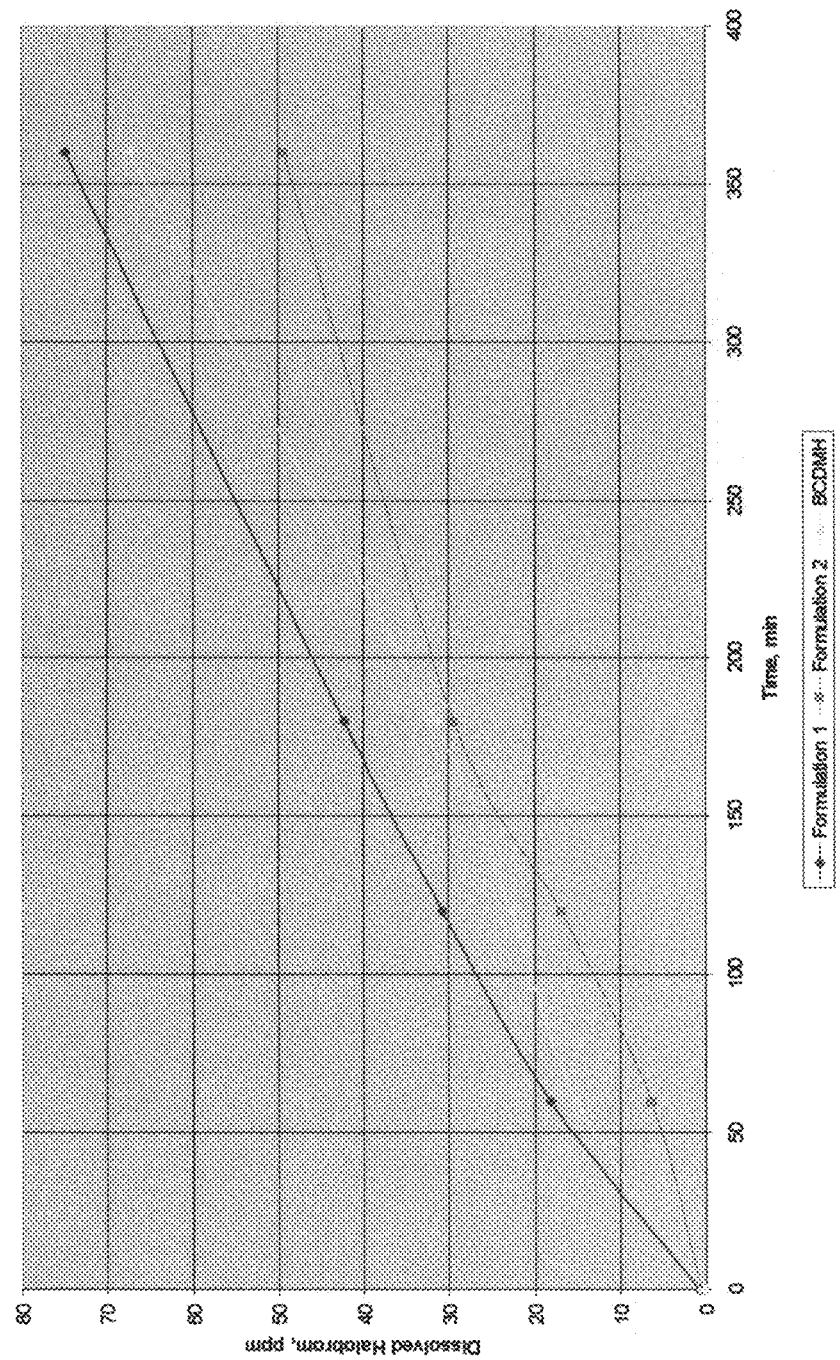
FIG. 2 presents comparative plots showing the dissolution rate of a tablet comprising BCDMH, Carnallite and eucalyptus oil (blue); a tablet comprising BCDMH, Carnallite and phenethyl acetate (pink); and a tablet comprising BCDMH only (yellow).

The solid formulations presented herein were further found to exhibit a dissolution rate of the sanitizer that is close to that of the sanitizer when utilized per se. As shown in FIG. 2, no significant change in the dissolution rate of a BCDMH-containing tablet was observed upon admixing the BCDMH with Carnallite and eucalyptus oil or phenethyl acetate.

While further conceiving the present invention, it was envisioned that forming a tightly packed solid object from the present solid formulations may contribute to both its chemical stability and to its practicality of use.

While reducing the present invention to practice, it was indeed found that the chemical stability of a tightly packed solid object is superior to non-compacted formulations. As demonstrated in the Examples section that follows, a compacted tablet was successfully formed from the solid formulations presented herein. Furthermore, exemplary tablets were put in an erosion device which resembles commonly used erosion devices used in pools and spas for adding chemicals in solid forms, and the compacted tablets maintained their integrity until completely dissolved. This surprisingly found quality is highly important for commercial products, since it avoids their premature breakage to smaller particles before final dissolution, which may clog water passageways in the water treatment plant/devices and may further affect the desired dissolution rate of the ingredients.

Another advantage of compacted bodies is the non-porous nature thereof which assists in keeping the formulation more chemically stable by attenuating air and moisture adsorption which is reduced to a minimum.

Thus, according to preferred embodiments of the present invention, the solid formulations presented herein have a form of a compacted body.

The morphology of the abovementioned compacted body can exhibit a random morphology such as, for example, the morphology of a prill, a nugget, a pellet, a flake or a granule, or exhibit an ordered, premeditated morphology such as, for example, the morphology of a pill, a caplet, a tablet, a wafer, a briquette, a puck or/and a block.

The shape of the compacted bodies of ordered morphologies may be a box, a sphere, a cube, an ellipsoid, a cylinder, a bar, a cone, a pyramid, a frustum, a prism, a torus, a shape similar to same, or any other pre-planned three dimensional shape.

As presented in the Examples section that follows, formulations which can be used in cases wherein the presence of a bath salt is not required or unwarranted, and therefore contain sanitizer(s), odoriferous substance(s) and no bath salt, have been prepared and molded into tablets. Such formulations are demonstrated in Examples 1, 2 and 3 hereinbelow.

As further presented in the Examples section that follows, formulations which can be used in cases wherein the presence of a bath salt is required or warranted, and therefore contain sanitizer(s) and bath salt(s), have also been prepared and molded into tablets. Such formulations are demonstrated in Example 4 hereinbelow.

As further presented in the Examples section that follows, formulations which can be used in cases wherein the presence of a bath salt is required or warranted, and therefore contain sanitizer(s), odoriferous substance(s) and bath salt(s), have been prepared and molded into tablets. Such formulations are demonstrated in Examples 6, 7, 8 and 9 hereinbelow.

As discussed hereinabove, certain water treatment conditions require a "burst" supply of some chemicals and a steady and continuous supply of others, depending on various situations at which the water in the circulating reservoir can be found. For example, a steep increase in the concentration of oxidizing or sanitizing agents, known as "pool shock", is needed in high-contamination conditions. Another example wherein a chemical is best introduced at once in the early stages of the water use is when the chemical is beneficial for the bathers and is chemically stable in the water, such as in the case of bath salts.

On the other hand, other chemicals, such as sanitizers and odoriferous substances, are constantly or periodically consumed, degraded or evaporated in or from the water. Such chemicals are therefore best introduced to the water in a steady and continuous mode.

Variations in chemical supply can be achieved by taking advantage of great differences in aqueous solubility between various chemicals in the same solid formulation, as presented in, for example, U.S. Pat. Nos. 3,873,685 and 6,863,830. Other techniques which can achieve the objective of controlled variability in chemical supply from one compacted body rely on separation of the chemicals into discrete layers and shaping the compacted body into various shapes and forms, such as presented in U.S. Pat. No. 5,759,974 and EP 1553162, wherein one ingredient of a formulation for use in lavatory cleansing and freshening blocks is engulfed by a shell made of another ingredient.

Thus, according to embodiments of the present invention, apart from having various morphologies and shapes, a compacted body comprising the solid formulations presented herein may have a layered structure.

The advantage of a multi-layered compacted body wherein several chemicals or mixtures of chemicals are combined in a layered fashion, is primarily to supply the appropriate chemical or mixture of chemicals at the propitious time according to the particular use and water treatment stage of the water reservoir. As the water conditioning process proceeds, a different formulation which is optimal for each particular stage of the water conditioning process is exposed and thus added to the water. Specifically, when an outer layer sheathes an inner layer in a layered structure, only the outer layer is exposed to the water and hence only the formulation present in that layer is added to the water. One can consider the temperature and rate of water flow over the compacted solid formulations, as presented herein, and calculate the time for complete dissolution of a layer. The time will depend on the solubility (dissolution rate) of that particular formulation in a layer, its surface area and its thickness. Accounting for all these easily attainable parameters, a multi-layered compacted body can be designed such that each layer is consumed by dissolution at a known and desired stage of the water conditioning plan. Furthermore, a multi-layered compacted body can be designed such that each layer comprises a different amount and/or ratio of the different components.

As presented in the Examples section that follows, formulations which contain sanitizer(s), odoriferous substance(s) and bath salt(s), and molded into multi-layered tablets have been prepared. Such formulations are demonstrated in Examples 10 and 11 hereinbelow.

As discussed herein, the solid formulations presented herein is a non-trivial combination of several sensitive and inherently incompatible chemicals, which, according to its intended use, is required to withstand storage while maintaining both chemical and mechanical stability during a prolonged time period.

While searching for an effective process for preparing such a formulation while overcoming the obstacles imposed by the incompatible characteristics of its components, the present inventors have found that subjecting bath salts such as those based on Camallite to in-process partial drying prior to formulating the salts in the presence of the sanitizers, beneficially affects the formulation process and hence enables the production of stable formulations of these ingredients. This partial drying was found, for example, to reduce the crystallization water content of the Camallite bath salt from 6 mole equivalents $H_2O$ to about 5.5 mole equivalents or less. Following this partial drying, these bath salts can be dry-blended with sanitizer(s) and optionally also with essential oils and the resulting mixture can be readily packed in tightly closed packages, for retaining the freshness and efficacy of all the ingredients of the formulation, including that of the odoriferous substance. Further still, it was found that by compacting the resulting solid formulation into compact bodies the water absorption of the formulation is reduced.

It was further found that the addition of an inorganic base to the solid formulations presented herein dramatically increases the stability of the formulations, even to the extent that by simply mixing the formulations ingredients, without pre-treatment such as the partial drying of the bath salt(s) described above, stable formulations are obtained.

As presented in the Examples section that follows, formulations which contain sanitizer(s), odoriferous substance(s), bath salt(s) and inorganic base(s), have been prepared. Such formulations are demonstrated in Example 12 hereinbelow.

Thus, according to another aspect of the present invention, there is provided a process of preparing a solid formulation that comprises a sanitizer and a bath salt, as described herein. The process, according to this aspect of the present invention, is effected by admixing the sanitizer(s) and the bath salt(s). The obtained admixture is referred to herein as "a first admixture".

Mixing of solids is a well established technique. Thus, admixing the components can be performed using any of the known techniques and any common solid-blending equipment. Preferably, the admixing is effected by rolling an inclined cylindrical or conical container having the solids for mixing placed therein. Gentle rolling circumvents the formation of dust and further grinding of the particles into undesirably too small particles. Furthermore, the container may be closed or partially closed so as to maintain certain physical conditions therein, such as temperature and humidity, during the mixing.

It is known that sanitizers, and especially halogen-releasing sanitizers such as BCDMH, by being strong oxidants, can react with organic compounds when exposed to moisture, leading to release of elemental bromine. As described hereinabove and further demonstrated in the Examples section that follows, it has been found that partially drying the bath salts prior to admixing with the sanitizer, abolishes this possibility, and hence further contributes to the stability of the formulation.

Thus, drying the bath salt(s) prior to admixing it with the sanitizer(s) achieves a more chemically stable formulation. Hence, according to preferred embodiments, the bath salt is at least partially dried before it is mixed with the sanitizer.

The phrase "partially dried", as used herein, refers to a substance which is subjected to an incomplete process in which part of the water of crystallization (water present in hydrated compounds upon solidification) is removed. Water of crystallization in chemical combination with a crystal is necessary for the maintenance of crystalline properties but is capable of being removed, at least partially, preferably by means of heating. Partial drying, according to the present invention, is achieved by applying moderate heat to a substance (e.g., the bath salt) in a static drying oven or while tumbling in a mixing cylinder of a dynamic drying oven for a pre-selected time period.

Preferably, the sanitizer is dry-blended with the bath salt that was previously subjected to this partial drying process. The dry blending and granulation process is thus carried out under dry conditions, common in the chemical industry, as described hereinabove.

Alternatively, the sanitizer is dry-blended with a bath salt in the presence of an inorganic base, as described hereinabove, whereby the bath salt can be used as is, without partially drying it before the admixing.

Once admixed, the resulting blend can be compacted immediately into compact bodies or can be stored in sealed packages, bins or silos under dried atmosphere until compacted. Storage can be effected for a time period of about 7 days, 14 days, 21 days, and up to 180 days and even more.

Hence, according to preferred embodiments of the present invention, the solid formulations presented herein have a form of a compacted body and the process further comprises compacting the abovementioned first admixture. Once compacted, and due to the non-porous nature of the resulting compacted bodies, the moisture adsorption is reduced to a minimum.

The compacting process can be any industrial process known in the art, including, for example, pressing, extrusion and molding. Such processes are effected by manual, semi-automatic and fully automatic machinery such as, for example, compression molding presses, transfer molding presses, injection/insert molding presses, thermoset extruders and extrusion-compression molding (ECM). Preferably, the compacting process is effected by pressing the present solid formulations in a mold.

As discussed hereinabove, solid formulations having a layered structure may beneficially controllably release their components. The layered structure can be prepared by techniques commonly known in the art.

In an example, when the compacted body is layered, the process can further comprise, prior to admixing the ingredients together, compacting the sanitizer(s) to thereby form a first layer; and compacting the bath salt(s) on top of the first layer to thereby form a second layer.

This process can be repeated several times so as to form a compacted body having more than two layers. Furthermore, the ingredients in each layer may vary discursively in a regular sequence, or any desired order, and the ratio between each ingredient may vary from layer to layer. For example, the first layer (core) may include a slow-dissolving sanitizer; the second (inner) layer may include a 50%:50% admixture of a slow-dissolving sanitizer and bath salts; and the last and most exposed (outer) layer may include a fast dissolving sanitizer. It should be evident that layered bodies having other ratios of the different components can be prepared.

Odoriferous substances may be added to the present solid formulations at various stages and to any ingredient. Nevertheless, another surprising effect which was encountered by the present inventors while reducing the present invention to practice, was that blending the odoriferous substances, which are typically hydrophobic and thus repel water, with the partially dried bath salts, can provide the salts with higher resistance to ambient moisture by partially sealing the surface of the salt crystals, thus facilitating their formulation with the sanitizer.

Thus, according to further embodiments of the present invention, the process of preparing solid formulations which comprise at least one odoriferous substance, further includes, prior to admixing the sanitizer(s) with the bath salt(s) and prior to any compacting process, blending the bath salt(s) with the odoriferous substance(s) to thereby obtain a second admixture; and admixing this second admixture with the sanitizer(s) to thereby obtain a third admixture. A "third admixture", as used herein, describes a mixture of a sanitizer, a bath salt and an odoriferous substance.

This third admixture can further be compacted, as described hereinabove, into one uniform compacted body or as one or more layers in a layered compacted body.

According to yet another aspect of the present invention there is provided a process of preparing a solid formulation which comprises one or more sanitizers and one or more odoriferous substances. The process, according to this aspect of the present invention is effected by blending the sanitizer(s) and the odoriferous substance(s) to thereby obtain an admixture thereof. The obtained admixture is referred to herein as "a fourth admixture".

Blending of a solid substance and a liquid substance which is not a solvent of the solid substance, such as in the case of a sanitizer and an odoriferous substance, can be achieved by any solid mixing technique known in the art. Preferably, blending is effected while using a tumbling cylinder which contains the solid substance and to which the liquid substance is added. The two substances are tumbled until at least a portion of the solid particles is coated with the liquid substance. This fourth admixture can further be compacted, as described hereinabove, into one uniform compacted body or as one or more layers in a layered compacted body.

In order to further overcome the hygroscopicity of the sanitizer(s) and/or the bath salt(s), the odoriferous substance can be sprayed through a fine jet over the surface thereof while the hygroscopic ingredients are still in a loose form (powder, granules and the like) concomitantly or subsequent to the blending step, thus avoiding their contact with the moisture in atmosphere. Formulations which are prepared by spraying the odoriferous substance are demonstrated in Examples 2 and 3 in the Examples section that follows.

As discussed hereinabove, the present solid formulations can be used in a circulating reservoir as a part of a comprehensive therapeutic protocol, which includes bathing in a warm solution that includes bath salts and/or odoriferous substances in combination with other pleasing and/or therapeutic substances and beneficial additives. The formulations described herein can therefore further comprise additives such as therapeutic substances which are customarily used to treat, or alleviate the symptoms of skin diseases such as, psoriasis vulgaris, generalisata, dermatitis, eczema, neurodermitis circumscripta, pruritus, prurigo, ichtyosis and sclerodermia circumscripta, parapsoriasis, acne vulgaris (indurata, conglobata), rosacea, skin rush, post-burn states, and/or locomotor disorders such as various forms of arthritis, psoriatic arthritis, vertebropathies, bechterev's disease and osteoarthrosis (cox arthrosis, gonarthrosis).

Further to additives which are added for the well-being of the bathers, other additives which are beneficial for the reservoir's systems and their operative state may be introduced to the water via the solid formulations presented herein.

Thus, according to preferred embodiments of the present invention, the solid formulations presented herein may further comprise one or more additional ingredients or additives, such as, for example, transdermally active therapeutic agents, therapeutic agents which are active by inhalation, skin conditioning agents, sunscreens, buffering agents, colorants and dyes, chelating agents, clarifiers, pearlescent agents, flocculenting agents, corrosion inhibitors, disintegrants, dispersants, dissolution control agents, foaming agents, fragrances and perfuming agents, pH-adjusting agents, scale inhibitors, sequesterants, surface-active agents, surfactants, UV blocking agents, water softeners, algaecides and algaestats, antifoaming agents, oils and any combinations thereof.

These additives may be added to the solid formulation at a content which ranges from about 0.001 weight percentage to about 10 weight percentages of total weight of the solid formulation, depending on their nature and intended use.

Thus, for example, therapeutically active agents such as transdermally active therapeutic agents, therapeutic agents which are active by inhalation, or skin conditioning agents, are preferably included in the formulations at a concentration that ranges from about 0.01 weight percentage to about 10 weight percentages, preferably from about 0.1 weight percentage to about 10 weight percentages, and more preferably from about 1 weight percentage to about 10 weight percentages.

The presently most preferred formulations according to the present embodiments comprise BCDMH as the sanitizer, Carnallite as the bath salt, if present, and eucalyptus oil, pine oil and/or phenethyl acetate as the odoriferous substance. Formulations comprising BCDMH, Carnallite and an inorganic base such as calcium hydroxide, with or without an odoriferous substance, are also preferred.

To achieve extended storage time and shelf-life, the solid formulations presented herein, having any form, size and shape as described herein, can be placed in an air-tight packaging material, preferably containing desiccant bags or packs. For example, tablet made from the solid composition can be stored indefinitely if seal-wrapped, e.g., in a water-soluble polyvinyl alcohol, thus allowing the product to be applied directly into the water without unwrapping so as to prevent human contact, or seal-wrapped in standard polyethylene, together with a desiccant bag (e.g., silica gel).

As discussed herein, the present solid formulations are highly suitable and beneficial for use for conditioning water of circulating reservoirs.

Thus, according to another aspect of the present invention, there is provided a method of conditioning water of a circulating reservoir, preferably a pool, a hot-tub, a whirlpool bathtub or a spa. The method, according to this aspect of the present invention, is effected by contacting the water with any of the solid formulations described herein.

Since the majority of the ingredients in the solid formulations are substantially water soluble, at least to some extent, the formulations are generally utilized by dissolving them in the water. The method by which the solid formulations are dissolved in the water depends on the size of the reservoir, namely, the amount of water to be conditioned, the type of water conditioning plan, the physical form of the solid formulations (e.g., size and shape) and the availability and type of suitable devices which form a part of the circulating reservoir and its water treatment system.

In practice, the solid formulations can simply be placed in the main water tank and left to dissolve, optionally with stirring the water in the tank. Preferably, this dissolution is effected by placing the solid formulations in a device which is specifically designated or especially designed to add dissolvable chemicals to the water of circulating reservoirs, such as an erosion feeder.

Hence, according to preferred embodiments, the method of water conditioning further includes placing the solid formulations presented herein in an erosion feeder which forms a part of the circulating reservoir. An exemplary erosion feeder, according to preferred embodiments of the present invention, is schematically illustrated in FIG. 1.

FIG. 1 presents a simplified illustration of a typical erosion feeder. An erosion feeder 10, designed to facilitate and control the dissolution of solid formulations identified for water conditioning in circulating reservoirs according to the present invention, is composed of a line 12 which feeds water from a main circulating reservoir tank 14 to a dissolution tank 16 which includes a perforated basket 18 filled with granules, pellets, tablets, pucks or blocks of a solid formulation 22, according to the present embodiments. Perforation in the perforated basket 18 allows the water in dissolution tank 16 to fill perforated basket 18 at substantially the same level as that of dissolution tank 16. Typically, perforated basket 18 is filled with formulation 22 to a level which is above the level of water in dissolution tank 16 so that as the tablets erode, more tablets are lowered by gravity and sink into the liquid of the tank, thereby continuing the dissolution process. An optional electrically controlled dissolution aid 24, in the form of a mechanical stirrer or an ultrasonic generator applies mixing or ultrasonic waves in order to assist the dissolution of solid formulation 22 in the liquid in dissolution tank 16. The water which contains dissolved solid formulation 22 exits dissolution tank 16 via line 26 and is pumped back into main circulating reservoir tank 14 by a pump 28.

It should be understood that the formulations exemplified herein as formulation 22 in FIG. 1 are illustrated as box-shaped blocks for clarity reasons, and can also be present in other solid forms, such as, for example, granules, pellets, tablets or pucks, as described herein.

Other exemplary devices for adding the present solid formulations for water conditioning according to preferred embodiments of the present invention are presented, for example, in U.S. Pat. No. 4,040,962 or 6,228,273, which are incorporated by reference as if fully set forth herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

BCDMH was obtained from the Dead Sea Bromine Group Ltd.

Eucalyptus oil was obtained from Emu Ridge (Australia) and Dan-Mor Ltd.

Pine oil was obtained from Dan-Mor Ltd.

Cineol and phenethyl acetate were obtained from Aldrich.

Carnallite-based bath salt was obtained from the Dead Sea Works.

Diethyl-p-phenylene diamine test kit was obtained from Merck Co.

Two counter-rotating rolls, on which a sealed container, containing the solid and liquid chemicals, was allowed to tumble, were used as a tumbling machine.

Tableting and strength measurements were performed using a tableting press and a Wilson's standard hardness/strength tester, obtained from the Instron Corp., Norwood, Mass. USA.

Example 1

Preparation of BCDMH/Eucalyptus Oil Tablets

Granulated BCDMH (199 grams) was blended by a tumbling machine with eucalyptus oil (0.1 gram) and the resulting admixture was pressed by a tableting machine into 20 grams cylindrical shaped tablets. The pressing was effected smoothly and the obtained tablets were easily extracted from the mould. The average breaking strength of the tablets was 13.5 $N/cm^2$, as measured on a Wilson Instruments standard hardness tester. After one week of aging at room temperature, the average strength of the tablets increased to 22.2 $N/cm^2$.

Example 2

Preparation of BCDMH/Fragrant Oil Tablet

Granulated BCDMH (199.5 grams) was coated with fragrant eucalyptus or pine oil (0.5 gram) by means of spraying through a compressed air-actuated jet over the granules rotating in an inclined bowl machine (Pascal Co. Ltd). The coated granules were pressed into tablets according to the technique presented in Example 1 hereinabove, and the resulting tablets exhibited similar strength characteristics as the tablets obtained in Example 1.

Example 3

Preparation of BCDMH/Fragrant Oil Tablet—Scaled Up Process

Granulated BCDMH (198 kg) and powdered calcium oxide (hydrated lime, 1 kg) were placed in a double cone, glass lined, 1000 liter rotating blender fitted with a jet for spray addition of liquids. The blender was rotated for 5 minutes at maximum speed of about 15 rpm in order to achieve a homogeneous blend of the two solids. Once a homogeneous blend was obtained, eucalyptus oil (1 kg) was sprayed over the solid mixture by means of a nitrogen stream while maintaining the rotational movement over a time period of 2-4 minutes. The rotation of the blender continued for additional 5 minutes and brought to a halt.

The free-flowing, oil-sprayed blend was removed and used as the feedstock for a tableting press machine, fitted with a mould which produced 20 grams, 1.25" diameter tablets.

The resulting tablets were imparted a pleasant eucalyptus odor that completely covered the pungent halogen odor. These tablets were used to disinfect water from in a 1000 liter whirlpool situated in an enclosed compartment, imparting to the water and the surrounding a pleasant scent that completely masked the unpleasant malodor of halogens and haloamines.

Example 4

Preparation of BCDMH/Carnallite Tablets

Carnallite-based bath salt (90 grams) was partly dried overnight at a mild temperature of 60-70° C., so as to reduce the molar water content from 6 mole equivalents to 5.5 mole equivalents. Thereafter the bath salt was blended with BCDMH (510 grams) in a tumbling machine for 30 minutes. The resulting admixture of 85% BCDMH and 15% Camallite-based bath salt was pressed into 20 grams tablets. The resulting tablets exhibited an average breaking strength 13.8 $N/cm^2$ which increased to an average breaking strength of 21.1 $N/cm^2$ after one week of aging.

Example 5

Hygroscopicity of BCDMH/Carnallite Tablets

BCDMH/Carnallite tablets, prepared from Carnallite-based bath salt that was subjected to various drying protocols, were prepared according to the procedure described in Example 4 hereinabove. The tablets were thereafter kept in the open on a bench top at room temperature and ambient humidity of 50% to 60% for a time period of 10 days. The weight of the dried tablets was recorded before (initial weight) and after the 10 days time period (final weight), and the results are presented in Table 1 below.

TABLE 1

| Drying temperature of the Carnallite-based bath salt (° C.) | Tablet weight (grams) | | Difference in weight (%) |
| --- | --- | --- | --- |
| | Initial | Final | |
| Not dried | 20.44 | 22.00 | +7.6 |
| 60 | 21.14 | 20.36 | −3.7 |
| 80 | 19.49 | 20.14 | +3.3 |

As can be seen in Table 1, the tablets prepared from non-dried Carnallite-based bath salt, or from Carnallite-based bath salt dried at 80° C. were prone to moisture absorption. The tablets prepared from Carnallite-based bath salt partially dried at 60° C. exhibited an opposite effect by losing total weight, thus demonstrating that partial drying of the Carnallite-based bath salt prior to admixing and pressing had a beneficial effect on the capacity of tablets to absorb moisture from the atmosphere.

Example 6

Stability of a BCDMH/Carnallite/Eucalyptus Oil Admixture

An admixture comprising Carnallite-based bath salt (15% by weight after partial drying at 70° C.), granular BCDMH (84% by weight) and eucalyptus oil (1% by weight) was prepared by blending in a tumbling jar at room temperature for 10 to 30 minutes. The resulting admixture was kept in a closed vessel for a time period of 11 days. Thereafter, the presence or absence of the sanitizer's breakdown product, $Br_2$, in the jar, easily perceptible as red-brown fumes, was visually determined. No indication of bromine release was recorded.

Example 7

Mechanical Strength of BCDMH/Pine Oil Tablets

The effect of fragrance content on the strength of BCDMH tablets was studied by preparing 20 grams BCDMH/pine oil tablets, essentially as described in Example 5 hereinabove, having various fragrance (oil) contents. The fragrance content was selected so as to maintain the pleasant smell imparted by the tablets. The tablets were prepared by pressing the admixtures of BCDMH and pine oil at a force of 45 kN.

The strength of the obtained tablets was determined essentially as described in Example 1 hereinabove immediately after pressing and after one week of aging, and the results are presented in the Table 2 below.

TABLE 2

| Fragrance content | Tablet strength N/cm$^2$ | |
|---|---|---|
| (weight percentage) | Immediate | After 1 week |
| 0.010 | 19.5 | 22.6 |
| 0.025 | 7.3 | 20.7 |
| 0.050 | 10.4 | 18.3 |

As can be seen in Table 2, the strength of the tablets immediately after pressing was adversely affected by increasing the oil content in the tablets. However, after one week of equilibration during the aging period, tablets of all oil content exhibited satisfying strength.

Example 8

Preparation, Stability and Dissolution of BCDMH/Carnallite/Eucalyptus Oil Tablets An admixture comprising BCDMH (85% by weight), Carnallite-based bath salt (14% by weight, dried at 70° C.) and eucalyptus oil (1% by weight) was prepared by tumbling the admixture for 30 minutes, and pressing the resulting granulated mash into 20 grams tablets essentially as described hereinabove.

The tablets were stored for three months in closed bags. At the end of this storage period, visual inspection of the bags confirmed the absence of elemental bromine, whereby the pleasant smell of the eucalyptus oil was maintained.

The tablets were subjected to the erosion action of water, simulating typical conditions found in a whirlpool hot tub, under the following conditions:

Tap water was heated thermostatically in a 30 cm crystallizing vessel to a temperature of 38-40° C. The water was cycled in and out of the vessel by a peristaltic pump at a constant flow of 0.5 liters per hour. The water level in the vessel was kept constant by an overflow outlet. The cycled water was directed through a plastic cartridge cage in which a 20 grams tablet was put. The available bromine level in the water was determined by the diethyl-p-phenylene diamine test (DPD, a test reagent commonly used to measure the amount of available chlorine and/or bromine in pool water), which measures both total and free bromine, as commonly known in the art. The level of available bromine accumulation versus time of sampling was used to calculate the dissolution rate.

After three hours of water circulation, the concentration of available bromine was 360 ppm (0.036%) and the water smelled pleasantly due to the eucalyptus oil infused therein. The calculated amount of eucalyptus oil was 0.0003 ppm, which is well within the recommended amount of fragrance in water of such facilities raging from 0.0001 to 0.0005 ppm.

Example 9

Stability of BCDMH/Carnallite/Fragrance Admixtures

Admixtures of BCDMH, Carnallite-based bath salt (dried at 70° C. unless otherwise indicated) and various fragrances at various concentrations thereof were prepared by tumbling all the ingredients together for 10-30 minutes. The granulated blends were stored in glass jars. One third of the jars were closed tightly and kept in ambient atmosphere, and the other two thirds were closed loosely. Half of the loosely closed jars (a third of the total number of jars) were stored in ambient atmosphere while the other half of the loosely closed jars were stored in a desiccator. Tests for bromine release in the jars were conducted as described hereinabove after a time period of 12 days, and the results are presented in Table 3 below.

TABLE 3

| Sample No. | BCDMH (wt %) | Carnallite (wt %) | Cineol (wt %) | Pine oil (wt %) | Eucalyptus oil (wt %) | Phenethyl acetate (wt %) | Bromine release after 12 days storage (qualitative) | | |
|---|---|---|---|---|---|---|---|---|---|
| | | | | | | | Tight | Loose | Desiccator |
| 1 | 99.95 | | 0.05 | | | | − | − | − |
| 2 | 99.90 | | 0.10 | | | | − | − | − |
| 3 | 99.99 | | | | 0.01 | | − | − | − |
| 4 | 99.95 | | | | 0.05 | | − | − | − |
| 5 | 99.90 | | | | 0.10 | | − | − | − |
| 6 | 99.99 | | | 0.01 | | | − | − | − |
| 7 | 99.95 | | | 0.05 | | | − | − | − |
| 8 | 99.90 | | | 0.10 | | | + | + | − |
| 9* | 99.90 | | | | | 0.10 | + | + | − |
| 10* | 85.00 | 14.90 | | | 0.10 | | − | − | − |
| 11* | 85.00 | 14.90** | | 0.10 | | | − | − | − |
| 12 | 85.00 | 14.90** | 0.10 | | | | − | − | − |
| 13 | 85.00 | 14.90 | | | 0.10 | | − | − | − |
| 14 | 85.00 | 14.90 | | 0.10 | | | + | − | − |
| 15 | 85.00 | 14.90 | 0.10 | | | | − | − | − |

*bromine release was determined after only 7 days of storage;
**as received from supplier (without partial drying)

As can be seen in Table 3, the release of bromine, which is indicative of the degradation of BCDMH, was not evident in samples which were kept in a desiccator. The only samples in which bromine release was recorded were admixtures without the Carnallite-based bath salt which had 0.1% of pine oil and phenethyl acetate, a widely used rose/fruity smelling colorless liquid, and a sample containing BCDMH, Carnallite-based bath salt and 0.1% pine oil.

Example 10

Preparation of Double-Layered Carnallite/Eucalyptus Oil and BCDMH Tablets

Carnallite-based bath salt (10 grams) was tumble-mixed for 30 minutes with eucalyptus oil (0.1 gram) in order to create a thin hydrophobic film over the Carnallite crystals.

10 grams of the eucalyptus oil coated Carnallite were put in a 30 mm diameter press mold and the mold was mounted on a pressing device to form a 10 grams tablet with a force of 45 kN. The plunger was removed and BCDMH granules (10 grams) were put in the mold, on top of the previously pressed Carnallite/eucalyptus oil tablet layer, and pressure was applied again with a force of 45 kN, to thereby form a double-layered tablet.

When subjected to dissolution in water, the Carnallite-based bath salt layer was more soluble in water than the BCDMH layer, and the bath salt layer eroded faster that the BCDMH layer; therefore these two chemicals were introduced into the water at two different rates to the circulating water.

A tablet such as described in the present example was subjected to the erosion action of the warm water of a whirlpool tub in a common erosion feeder (also known as a "brominator"). The Carnallite-based bath salt layer was dissolved quickly so as to reach the required concentration of salts and fragrance in water (about 1% and 0.01% respectively) while the BCDMH layer kept acting by slowly dissolving according to the bromine demand of the water.

Example 11

Preparation of Triple-Layered Carnallite/Eucalyptus Oil and BCDMH Tablet

In order to minimize the surface area of the bath salt which is exposed to the atmosphere, the Carnallite-based bath salt layer was pressed between two layers of BCDMH.

BCDMH granules (5 grams) were put in the mold, in a 30 mm diameter press mold, and the mold was mounted on a pressing device to form a 5 grams tablet with a force of 45 kN. Thereafter the plunger was removed and 10 grams of the eucalyptus oil coated Carnallite crystals were put in the mold, on top of the previously pressed BCDMH tablet layer, and pressure was applied again with the force of 45 kN so as to form a double-layered tablet. The plunger was removed and another portion of BCDMH granules (5 grams) was put in the mold, on top of the double-layered tablet, and pressure was applied again with the force of 45 kN thereby forming a triple-layered tablet, having a bath salt/fragrance layer "sandwiched" between two layers of the biocide.

Example 12

Stability of a BCDMH/Carnallite/Eucalyptus Oil/Calcium Hydroxide Admixture

An admixture comprising Carnallite-based bath salt (about 15% by weight, used as is, without drying), granular BCDMH (about 84% by weight), eucalyptus oil (1% by weight) and calcium hydroxide (0.1% by weight) was prepared by blending in a tumbling jar at room temperature for 10 to 30 minutes. The resulting admixture was kept in a closed vessel for a time period of 14 days. Thereafter, the presence or absence of the sanitizer's breakdown product, $Br_2$, in the jar, easily perceptible as red-brown fumes, was visually determined, indicating no bromine release.

Example 13

Dissolution of Tablets Containing BCDMH in the Presence or Absence of Carnallite and Eucalyptus Oil or Phenethyl Acetate The dissolution rate of tableted solid formulations containing BCDMH alone, BCDMH, Carnallite and eucalyptus oil and BCDMH, Carnallite and phenethyl acetate was tested. The results, presented in FIG. 2, show no significant difference in the dissolution rate of all the tested formulations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A solid formulation consisting of at least one oxidizing sanitizer, at least one bath salt, at least one odoriferous substance and optionally at least one inorganic base, wherein said oxidizing sanitizer is a halogen-releasing sanitizer, and wherein said bath salt is Carnallite or a Carnallite-based salt.

2. The solid formulation of claim 1, being chemically stable for a time period of at least 7 days upon storage at a temperature that ranges from 0° C. to 50° C. and an ambient humidity that ranges from 20% to 65%.

3. The solid formulation of claim 1, having a form of a compacted body.

4. The solid formulation of claim 1, being a granulated formulation.

5. The solid formulation of claim 1, wherein said halogen-releasing sanitizer is BCDMH.

* * * * *